US005583285A

United States Patent [19]
Hahn et al.

[11] Patent Number: 5,583,285
[45] Date of Patent: Dec. 10, 1996

[54] METHOD FOR DETECTING A COATING MATERIAL ON A SUBSTRATE

[75] Inventors: Mark H. Hahn, Indianapolis; Mary L. Patterson, Carmel, both of India.

[73] Assignee: Lucent Technologies Inc., Murray Hill, N.J.

[21] Appl. No.: 346,454

[22] Filed: Nov. 29, 1994

[51] Int. Cl.$^6$ .................................................. G01N 13/02
[52] U.S. Cl. ........................................................ 73/64.52
[58] Field of Search ........................... 73/64.52, 64.48; 356/138

[56] References Cited

U.S. PATENT DOCUMENTS

| | | | |
|---|---|---|---|
| 3,618,374 | 11/1971 | Miller | 73/64.52 |
| 3,696,665 | 10/1972 | Poppe et al. | 73/64.48 |
| 4,050,822 | 9/1977 | Grat | 73/64.52 |
| 4,373,656 | 2/1983 | Parker, Jr. et al. | . |
| 4,688,938 | 8/1987 | Demoulin et al. | 356/138 |
| 5,080,484 | 1/1992 | Schneider et al. | 356/138 |
| 5,115,677 | 5/1992 | Martin et al. | 73/64.48 |
| 5,137,352 | 8/1992 | Blitshteyn et al. | 73/64.52 |
| 5,300,670 | 5/1994 | Kobayashi | 556/454 |

FOREIGN PATENT DOCUMENTS

| | | | |
|---|---|---|---|
| 87159 | 5/1986 | Japan . | |
| 157813 | 7/1991 | Japan . | |
| 31740 | 2/1992 | Japan | 73/64.52 |
| 223481 | 8/1993 | Japan . | |

OTHER PUBLICATIONS

Yoshida et al., *A study on the orientation of Imidazoles on Copper as Corrosion Inhibitor and possible Adhesion Promoter for Electrical Devices*, J. Chem. Phys., vol. 78, No. 11, 6960–6969 (Jun. 1, 1983).

Tompkins et al.,i *The Interaction of Imidazole, Benzimidazole and Related Azoles with a Copper Surface*, Surface and Interface Analysis, vol. 4, No. 6, 261–266 (1982).

Guttierrez et al., *Individual and Joint Kinetic Fluorimetric Determination of Imidazole and 4–Methylimidazole*, Microchemical Journal 34, 332–339 (1986).

Zhang et al., *The formation of Composites from Imidazole Polymer with Epoxy Resins*, Applied Surface Science 72, 67–72 (1993).

Xue et al., *In Situ Studies of Coatings on Metal Wires by FT–IR External Reflectance Spectroscopy*, Applied Spectroscopy, vol. 41, No. 7, 1172–175 (1987).

Bonomo et al, *EPR Reinvestigation of the Copper (II) —Imidazole System*, Inorg. Chem., vol. 27, No. 14, 2510–2512 (1988).

Sato et al., *Effects of Ionic Strength on the Structure of Cu (II). Poly(vinylimidazole) and Cu(II). Imidazole Complexes in Aqueous Solution*, Makromol. Chem. 180, 699–704 (1979).

Xue et al.,,, i *Chemical Reaction of Metallic Copper with Imidazole*, J. Chem. Soc. Dalton Trans., 1487–1488 (1988).

Holze, R., *The Electrosorption of Imidazole on a Gold Electrode as Studied with Spectroelectrochemical Methods*, Electrochemica Acta. vol. 38, No. 7, 947–956 (1993).

Thomas et al., *Correlation of Surface Wettability and Corrosion Rate for Benzotriazole–Treated Copper*, J. Electrochem. Soc., vol. 139, No. 3, 678–685 (Mar. 1992).

Enthone–Omi Inc., Customer Bulletin, Entek® Cu 56/cu–56HF *Nitric Acide Drop Test*, (Mar. 21, 1990) and Entek® Plus CU–106A, *Presence Analysis*.

Pirie et al., *The Measurement of Wettability, A Simple Method For Contact Angle Determinations*, Journal of Chemical Education, vol. 50, No. 10, pp. 682–684, Oct. 1973.

Ryley et al., *A New Method of Determining the Contact Angle Made by a Sessile Drop Upon a Horizontal Surface (Sessile Drop Contact Angle)*, Journal of Colloid and Interface Science, vol. 59, No. 2, pp. 243–251, Apr. 1977.

*Primary Examiner*—Hezron E. Williams
*Assistant Examiner*—Daniel S. Larkin

[57] ABSTRACT

A method for detecting the presence of a coating material, particularly an organic solderability preservative, such as imidazole, on a copper substrate includes placing a test droplet on the surface of the substrate, forming an image of the droplet and measuring the contact angle between the wall of the droplet and the surface of the substrate.

6 Claims, 1 Drawing Sheet

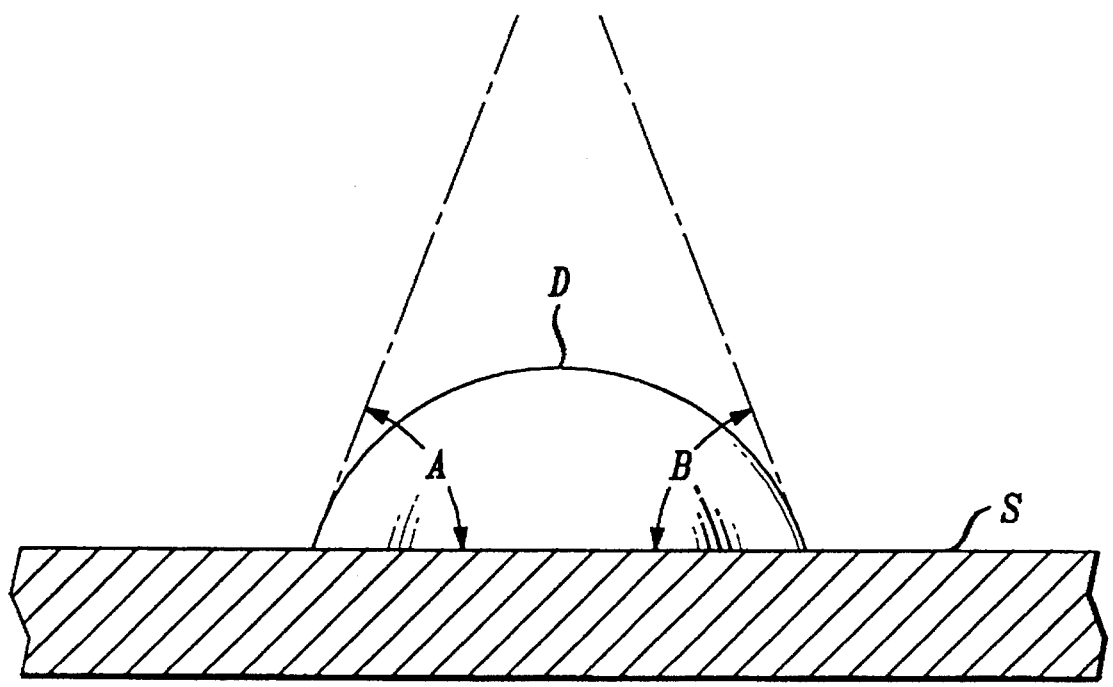

METHOD FOR DETECTING A COATING MATERIAL ON A SUBSTRATE

BACKGROUND OF THE INVENTION

1. Field of the Invention

This invention relates to a method for detection of a coating material on a substrate and more particularly to a method for detecting and/or distinguishing the presence of an organic solderability preservative on a copper substrate.

2. Description of the Related Art

Bare copper surfaces oxidize on exposure to air and develop a patina containing copper hydroxide and various other copper compounds. Even invisibly thin coatings of this patina are sufficient to interfere with the ability of solder to wet and form a bond with the copper surface. Surface oxidation renders a copper substrate non-solderable, and unusable. Hence, newly etched copper used in electronic circuit boards is coated with a solderability preservative.

Use of imidazole as an organic solderability preservative ("hereinafter, "OSP") is described in U.S. Pat. No. 4,373,656, herein incorporated by reference. Other OSP's are also known and include various azole derivatives such as benzimidazole, benzotriazole, and alkyl imidazoles. OSP's generally work by forming a complex with copper, which prevents further surface oxidation without diminishing the solderability of the surface.

Detection of the OSP should be performed immediately after the coating process as a process control step, or in the field prior to the soldering process. One problem arises from the fact that the OSP coating is present in very low quantities. Very often, the OSP coating has a thickness of only one monomolecular layer of OSP-copper complex.

A large percentage of the printed circuit boards currently being used are coated with imidazole. Imidazole deposition is a delicate process which would be dramatically improved with a detection technique used as a process monitoring tool. Such a technique should meet three criteria: it should be non-destructive, it should be sensitive enough to detect minute levels of the OSP, and it should be simple to perform with minimal training of the personnel performing the inspection procedure.

Various attempts have been made to achieve such a method: FT-IR reflective techniques, use of a quartz crystal oscillator microbalance, fluorimetry, viscometry, spectroscopy, ESR techniques, XPS, IR, and electrochemical methods such as voltammetry, tensammetry, and SERS. Chemically, imidazole has been detected by its reaction with epoxy compounds. Absence of OSP has also been detected by nitric acid and silver nitrate drop tests.

Many of these methods do not meet the above criteria for a non-destructive, sensitive method which is easily learned by new personnel. Some of the methods require years of advanced study to properly perform the tests and accurately interpret the results with acceptable efficiency. Also, some of the methods mentioned above are for use in aqueous solutions which require a significant area of sample preparation relative to the surface area of the printed wiring product.

We have discovered an improved technique for detecting an OSP coating especially imidazole on copper. The method is non-destructive, sensitive enough to detect monomolecular layers of coating, and employs relatively simple instrumentation with which a high level of operator skill can be acquired in a matter of hours. The technique is both simple and accurate and may be broadly applied to various types of coating materials and substrates.

SUMMARY OF THE INVENTION

A method for detecting the presence of a coating material, especially an organic solderability preservative, on a substrate is disclosed herein. The method includes the steps of placing a droplet of test liquid on the surface of the substrate (e.g. a copper surface), and comparing a surface feature of the droplet against a predetermined standard. Generally, an image is formed of the droplet and the contact angle defined by the wall of the droplet and the surface of the metal substrate is measured and compared with known values of contact angles for the particular coating material and bare substrate surface. The method is particularly applicable to imidazole coated copper substrates used for printed circuits. Other organic solderability preservatives may also be detected by the method described herein.

BRIEF DESCRIPTION OF THE DRAWINGS

FIG. 1 is a diagrammatic representation of the imaged test droplet on a metal substrate.

DETAILED DESCRIPTION OF PREFERRED EMBODIMENT(S)

The method of the present invention relies on the fact that the surface features of a droplet of liquid vary depending on the surface of the substrate upon which the droplet is placed. The method includes the steps of placing a droplet of test liquid on the surface of the substrate (e.g. a copper surface), and comparing a surface feature of the droplet against a predetermined standard. Generally, an image is formed of the droplet and the contact angle defined by the wall of the droplet and the surface of the metal substrate is measured and compared with known values of contact angles for the particular coating material and bare substrate surface. The contact angle is a convenient surface feature to examine to achieve a quantifiable determination.

Because this method is especially advantageous for measuring OSP, especially imidazole, on copper substrates used in printed circuit boards, the method will be described in terms of imidazole coatings on copper. However, it should be understood that the present method can be used to detect other OSP's and should not be limited to copper substrates. Other azole derivatives useful as OSPs include benzotriazole, benzimidazole, 2-methyl benzimidazole, 2-phenylimidazole, and alkyl imidazoles such as 2-undecyl imidazole and 2-heptadecyl imidazole. Other metal substrates can be iron or aluminum.

The first step of the method is to dispense a droplet of water on the copper surface to be tested. The droplet preferably has a volume of from about 0.1 to about 30 microliters, more preferably from about 0.5 to about 10 microliters, and most preferably from about 1.5 to about 2.5 microliters. Such a droplet can be dispensed by means of a microliter syringe. Typically a 100 microliter syringe is used, but other sizes of syringe may also be employed. The needle preferably has a 90° bevel at the tip to allow good contact between the droplet and the surface to be tested, and the barrel of the needle is held perpendicular to the sample surface. The volume of the dispensed droplet may be easily controlled using a repeater dispenser, which allows the rotation of a screw to activate the syringe plunger. Approximately 1.5 microliters of fluid is dispensed from the syringe while the sample surface is not in proximity of the droplet. The droplet will hang from the syringe at this point. The surface is then slowly brought into contact with the bottom of the droplet surface by actuating a positioner on which the sample rests. An additional 0.5 microliters of fluid is then dispensed, after which the sample is lowered.

Preferably, deionized water is used, although ordinary tap water may also be used. Optionally, other liquids such as glycerol may be used instead of water. Use of liquids other than water, while still yielding a detectable difference between a bare clean copper and OSP-coated copper, will result in different absolute contact angles.

Detection of imidazole on the copper surface is performed by measuring the contact angle of the droplet with the copper surface. This is preferably accomplished through visual inspection by forming an image of the droplet with any appropriate combination of optics and visually measuring the contact angles of the droplet as depicted in the image. The measurements are preferably made within 30 seconds of dispensing the test droplet.

Referring to FIG. 1, a diagrammatic illustration of the imaged test droplet D is shown deposited on the surface of substrate S. Angles A and B are the contact angles as defined by the angle between the surface of the substrate and a line tangent to the surface of the droplet at the point where the droplet contacts the surface of the substrate. Under ideal conditions angles A and B should be equal. However, lack of droplet symmetry may be caused by, for example, deviation of the surface from a true horizontal position or from true flatness. Under such conditions the shape of the droplet may be skewed, thereby resulting in dissimilar angles. Accordingly, it is advisable to measure the contact angles on opposite sides.

EXAMPLES

In the examples set forth below the samples of imidazole coated copper and bare copper were prepared shortly before performing the test. The longer the time interval between sample preparation and subsequent testing, the more inaccuracy is introduced. Freshly prepared samples avoid complications caused by oxidation of the bare copper and modification of the coating by complexing or other processes. Accordingly, to achieve the most accurate and consistent results testing should be performed within about 30 minutes from sample preparation and more preferably within 5 to 20 minutes.

EXAMPLE 1

A freshly etched copper surface was coated with imidazole in a manner similar to that described in U.S. Pat. No. 4,373,656. This test was performed within 5–10 minutes after imidazole coating and was carried out under ambient laboratory conditions 25° C. and 50% relative humidity. A droplet of deionized water approximately two microliters in size was placed on the imidazole coated copper surface and an image of the droplet was obtained by using a video contact angle system designated as VCA 2000, which is available from Advanced Surface Technology, Inc. located at Nine Linnell Circle, Billerica, Mass. 01821-3902. Standard operating parameters were used. Left and right contact angles were observed to insure symmetry of the droplet. This testing procedure was performed a number of times sufficient to obtain a statistically relevant average measurement at 95% confidence levels. The mean contact angle is set forth below in Table I.

EXAMPLE 2

Bare uncoated samples of copper were prepared for comparison purposes. The uncoated copper surfaces were prepared by a standard etching treatment comprising dipping of the copper sample in the following solutions, in the order given, for one minute in each bath:

1. Dipping in 5 wt % sodium hydroxide (NaOH) in deionized water.
2. Dipping in deionized water.
3. Dipping in a mild aqueous etch solution comprising 1.5 lbs of sodium persulfate per gallon of water held at about 90° F. with mild agitation.
4. Dipping in deionized water.
5. Stabilization by dipping in a bath comprising 50% deionized water and 50% stock solution of 68.6 grams of 85% phosphoric acid solution, 7.5 grams ethylene glycol, and 23.9 grams distilled water.
6. Dipping in deionized water.
7. Drying in warm air.

The uncoated copper surfaces were tested within 5–10 minutes of their preparation using deionized water with the technique and equipment and under the same laboratory conditions as set forth above with respect to Example 1. A sufficient number of samples were prepared and tested to obtain a statistically relevant average measurement at 95% confidence level. The mean contact angle is set forth below in Table I.

TABLE I

| Contact Angle Measurements | |
|---|---|
| | Mean Contact Angles |
| Example 1 (imidazole coated copper) | 54.5 ± 5.4° |
| Example 2 (uncoated copper) | 25.8 ± 4.5° |

As can be seen from the above Examples, the imidazole coated copper surface results in a substantially different contact angle than bare copper with the use of deionized water as the test droplet. As mentioned above, different test liquids and OSP's produce different characteristic contact angles. These characteristic angles can be determined beforehand by standardized measurements, then used to detect and distinguish OSPs on copper surfaces by a simple measuring procedure.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. A method for monitoring a process for coating a copper substrate with a layer of organic solderability preservative, comprising:

a) providing a copper sheet;
   b) etching a surface of said copper sheet;
   c) coating said copper surface with an organic solderability preservative;
   d) placing a droplet of test liquid on said coated surface within 10 minutes after coating said copper substrate;
   e) obtaining an image of the droplet;
   f) measuring the contact angle defined by a wall of the droplet and the coated surface within about 30 seconds after placing said droplet on said coated substrate; and
   g) comparing the measured value of the contact angle with a predetermined standard comprising known values of contact angles.

2. The method of claim 1 wherein said organic solderability preservative is imidazole.

3. The method of claim 1 wherein said test liquid is selected from the group consisting of water and glycerol.

4. The method of claim 1 wherein said droplet has a volume of from about 0.1 to about 30 microliters.

5. The method of claim 1 wherein said step of measuring the contact angle comprises measuring both a left contact angle and a right contact angle on said image of the droplet wherein said image is obtained from a video observation system.

6. The method of claim 1 wherein said process is for making a printed circuit board.

* * * * *